(12) United States Patent
Fukutomi et al.

(10) Patent No.: US 7,900,516 B2
(45) Date of Patent: Mar. 8, 2011

(54) ULTRASONIC FLAW DETECTION APPARATUS AND ULTRASONIC FLAW DETECTION METHOD

(75) Inventors: Hiroyuki Fukutomi, Tokyo (JP); Shan Lin, Tokyo (JP); Tetsuo Fukuchi, Tokyo (JP)

(73) Assignee: Central Research Institute of Electric Power Industry, Tokyo (JP)

( * ) Notice: Subject to any disclaimer, the term of this patent is extended or adjusted under 35 U.S.C. 154(b) by 297 days.

(21) Appl. No.: 12/304,912

(22) PCT Filed: Jul. 6, 2007

(86) PCT No.: PCT/JP2007/000740
§ 371 (c)(1),
(2), (4) Date: Dec. 15, 2008

(87) PCT Pub. No.: WO2008/007460
PCT Pub. Date: Jan. 17, 2008

(65) Prior Publication Data
US 2009/0199642 A1      Aug. 13, 2009

(30) Foreign Application Priority Data

Jul. 11, 2006 (JP) ................. 2006-190016
Oct. 20, 2006 (JP) ................. 2006-286202
Jan. 19, 2007 (JP) ................. 2007-010134

(51) Int. Cl.
*G01N 29/07* (2006.01)
(52) U.S. Cl. ............... 73/598; 73/599; 73/600; 73/602; 73/627
(58) Field of Classification Search .......... 73/598, 73/599, 600, 602, 620, 627, 628, 649
See application file for complete search history.

(56) References Cited

U.S. PATENT DOCUMENTS
4,137,779 A * 2/1979 Wustenberg et al. .......... 73/627
(Continued)

FOREIGN PATENT DOCUMENTS
JP       64-46644 A       2/1989
(Continued)

OTHER PUBLICATIONS

Takeshi Mihara et al., "Laser Choonpaho o Mochiita Time of flight diffraction Sokutei", Technical Report of IEICE, vol. 102, No. 307, Sep. 12, 2002, pp. 39.

(Continued)

*Primary Examiner* — Jacques M Saint Surin
(74) *Attorney, Agent, or Firm* — Notaro, Michalos & Zaccaria P.C.

(57) ABSTRACT

To simply and accurately determine the position of an edge, the depth or the height of a flaw including a surface crack, a corroded portion near the surface layer of a thick specimen, and a minute damage.

An ultrasonic flaw detection method causes an ultrasonic wave 16 to be incident on a specimen 6 from an oblique direction, detects a diffracted wave 17 generated at an edge of a flaw 20 in the specimen 6 above the flaw, and determines the position of the edge of the flaw 20 from a front surface 13 of the specimen 6 using a triangular method from an entire beam path Wt of a component 18, which directly propagates above the flaw 20, of the diffracted wave, the entire beam path passing through the flaw from the position of incidence of the component 18, and an interval S between the position of incidence and the position of detection of the ultrasonic wave or from the difference $(t_r - t_s)$ between the propagation time of a surface wave 15, to which the above relations reflect, to reception and the propagation time of the diffracted wave 18, which directly propagates above the flaw, to reception.

11 Claims, 6 Drawing Sheets

U.S. PATENT DOCUMENTS

| | | | | | |
|---|---|---|---|---|---|
| 4,299,128 | A | * | 11/1981 | Gruber | 73/627 |
| 4,577,505 | A | * | 3/1986 | Jestrich et al. | 73/629 |
| 4,785,667 | A | * | 11/1988 | Miyajima et al. | 73/618 |
| 5,005,420 | A | * | 4/1991 | Miyajima | 73/629 |
| 5,497,662 | A | * | 3/1996 | Dykes | 73/634 |
| 7,240,554 | B2 | * | 7/2007 | Berke | 73/602 |
| 2006/0230831 | A1 | * | 10/2006 | Berke | 73/602 |
| 2009/0007678 | A1 | * | 1/2009 | Fukutomi et al. | 73/598 |
| 2009/0217763 | A1 | * | 9/2009 | Yamano | 73/622 |

FOREIGN PATENT DOCUMENTS

| | | |
|---|---|---|
| JP | 2503139 Y2 | 4/1996 |
| JP | 2001-228126 A | 8/2001 |
| JP | 2002-62281 A | 2/2002 |
| JP | 3294148 B2 | 4/2002 |
| JP | 2004-117137 A | 4/2004 |
| JP | 2005-43139 A | 2/2005 |

OTHER PUBLICATIONS

Takeshi Mihara, "TOFD-ho no Genri to BS7706", Journal of JSNDI, vol. 49, No. 12, Dec. 1, 2000, pp. 802 to 805.

Lin Shan et al., "SPOD-ho ni yoru Kizufukasa no Sokutei—Sono I:SPOD-ho no Teian-", Dai 13 Kai Choonpa ni yoru Hihakai Hyoka Symposium Koen Ronbunshu, Jan. 24, 2006, p. 11.

Tetsuo Fukuchi et al., "Development of a Multi-Beam Laser Ultrasonic Inspection System and Its Application on Flaw Sizing", CRIEPI Report, Aug. 2006.

Lin Shan et al., "SPOD-ho ni yoru Kizufukasa no Sokutei—Sono I:SPOD-ho no Teian-", Dai 13 Kai Choonpa ni yoru Hihakai Hyoka Symposium Koen Ronbunshu, Jan. 24, 2006, p. 12.

Quantitative Nondestructive Evaluation vol. 25, Jul. 31-Aug. 5, 2005.

B.T. Cross et al., "Delta technique extends the capabilities of wells quality assurance", British Journal of N.D.T., Dec. 1969.

* cited by examiner

ULTRASONIC FLAW DETECTION APPARATUS AND ULTRASONIC FLAW DETECTION METHOD

TECHNICAL FIELD

The present invention relates to an ultrasonic flaw detection method and an ultrasonic flaw detection apparatus. More particularly, the present invention relates to an ultrasonic flaw detection method and an ultrasonic flaw detection apparatus suitable for detecting the position of an edge of a flaw including a surface crack, a corroded portion near the surface layer of a thick specimen, and a minute flaw, the depth of the flaw, or the height of the flaw from a back surface.

BACKGROUND ART

Conventionally, an ultrasonic flaw detection test is executed to nondestructively inspect the depth of a flaw in a surface crack of a weld of a thick pipe such as a weld of a pipe of an atomic power plant and the depth and the position of a flaw including a corroded portion near a surface layer and a minute flaw, the height of a flaw from a back surface, and the like. In the nondestructive inspection to the weld of the thick pipe, needs for accurately measuring the height, the depth, the size of a flaw and the like are increased in addition to simply detecting whether or not a flaw is present. In the sizing of a defect, since it is indispensable to detect a flaw generation edge and a flaw termination edge with a pinpoint accuracy, it is recently contemplated to apply ultrasonic flaw detection methods such as a phased array method, a TOFD method, i.e., Time of Flight Diffraction method, an angle flaw detection method, and the like.

Figure 13:
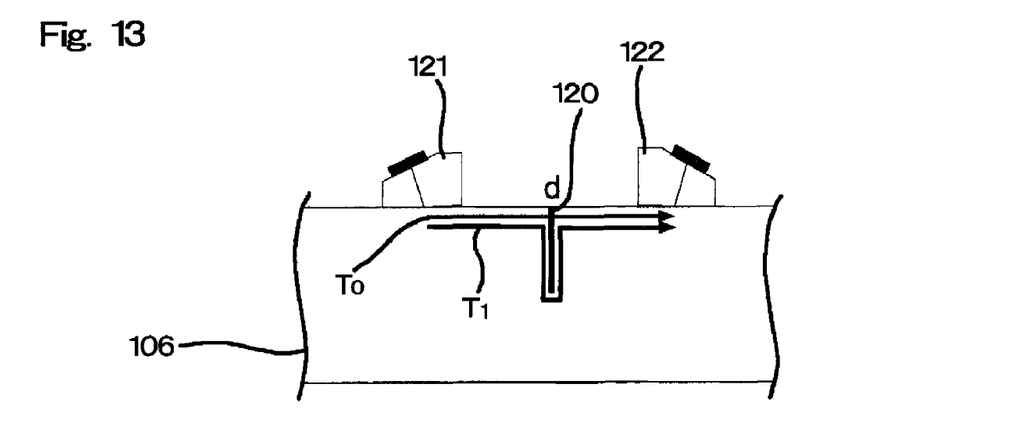
FIG. 13 is a view for explaining a method of estimating the flaw depth of a surface crack by a conventional TOFD method.

For example, the TOFD method making use of a surface wave is generally used to estimate the depth of a flaw of a surface crack (Non-Patent Document 1). As shown in FIG. 13, according to the TOFD method, the difference in paths is generated between the beam path $T_0$ of a surface wave when a crack is not present and the beam path $T_1$ of the surface wave when a crack is present. Thus, after the beam path $T_0$ of the surface wave when the crack is not present is previously determined and the beam path $T_1$ of the surface wave when the crack is present is determined, a flaw depth d is estimated from the relation shown in Expression 1. The beam path means a distance in which a beam passes between a probe on a transmission side and a probe on a reception side.

$$d = \tfrac{1}{2}(T_1 - T_0) \quad (1)$$

Further, the flaw height may be measured by an angle flaw detection method using an angle probe (Non-Patent Document 2).

Further, the inventors have proposed an ultrasonic measuring method called an SPOD method, i.e., Short Path of Diffraction method, which is suitable for measuring a flaw in the periphery of a weld of austenite-based stainless steel and Inconel (registered trademark of Special Metals Corporation) which is mainly used in an in-furnace structure, a circulating piping, and the like of a primary structure of an atomic power plant, in particular, the height of a flaw in a back surface opening (Non-Patent Document 3). In the SPOD method, a flaw height is determined from the difference between the arriving times of a component, which directly propagates above a flaw, and a component which propagates above the flaw after it is reflected on the back surface of a specimen in such a manner that an angle probe is combined with an a normal probe, an ultrasonic pulse is caused to be incident on a flaw in the specimen from an oblique direction, and a diffracted wave generated at an edge of the flaw is received by the normal probe above the flaw.

Non-Patent Document 1: The Japanese Society for Non-Destructive Inspection, "Flaw Height Measuring Method by TOFD Method Standardized by The Japanese Society for Non-Destructive Inspection", published on Dec. 1, 2001

Non-Patent Document 2: The Japanese Society for Non-Destructive Inspection, "Flaw Height Measuring Method by Tip Echo Techniques Standardized by The Japanese Society for Non-Destructive Inspection", published on Jun. 1, 1997

Non-Patent Document 3: "Proposal of Simple Flaw Sizing Method in Ultrasonic Flaw Detection Test", Program & Abstracts of Second Academic Lecture of Conservation Society of Japan, pp 21-26, distributed on Jul. 8, 2005

DISCLOSURE OF THE INVENTION

Problems to be Solved by the Invention

However, a surface crack is generated often in a shape changing portion of a structure in which stress concentration is liable to be caused, for example, a pipe stand of a thick pipe, and a weld in which thick pipes such as T-shaped joints and the like are welded to each other at an angle. It is difficult to detect a surface flaw located in the shape changing portion by disposing two probes so as to clamp the surface crack. Further, it is impossible for the TOFD method to accurately estimate a flaw because the echo of a surface wave to be received is weak. Accordingly, it is difficult to detect the surface crack from an opening and to determine the depth thereof using the TOFD method. In particular, the TOFD method has a problem in that it cannot be used for austenite-based stainless steel, Inconel, and the like, which are mainly used for an in-furnace structure, a circulating piping, and the like of a primary structure of an atomic power plant the depth of a flaw of which is required to be measured by a nondestructive manner, because the TOFD method entails a large amount of attenuation and noise.

Further, even when a lower edge of a surface crack is detected using an angle flaw detection method, since the echo of a diffracted wave from the lower edge of the flaw cannot be detected, the depth of the flaw cannot be estimated. This is because the echo of a diffracted wave having such a degree that it can be detected cannot be obtained since the energy of the diffracted wave in an upper oblique direction is weak from the beginning as well as diffused and attenuated by an increase in length of a beam path.

Further, when a corroded portion exists in a specimen, since the corroded portion and a healthy portion in the periphery thereof have the same physical properties from the beginning and the physical properties thereof are not greatly changed even if they are corroded, an ultrasonic wave almost entirely passes through the interface therebetween, and thus a generated reflected wave and a generated diffracted wave become weak. Accordingly, since it is difficult for ordinary ultrasonic measuring methods such as the TOFD to detect the boundary surface between a corroded portion and a healthy portion, it is difficult for the methods to detect the presence or absence of a corroded portion which does not appear on a front surface by the nondestructive inspection and further to detect the depth of the corroded portion even if it appears on the front surface. This is the same in closed defects in general such as an initial fatigue crack, a closed crack, a creep void of a grain boundary, and a fine exfoliation when they appear in the specimen as a group of small defects (hereinafter, called a minute defect) and the like which are much smaller than the wavelength of an incident wave. A block of the minute defects and the like can be determined as corroded and deteriorated portion (hereinafter, called a corroded portion), and a conventional ultrasonic flaw detection method cannot determine the depth position of the boundary surface between the corroded portion and the healthy portion.

Further, it has been found that when the depth of a flaw from the front surface of a specimen or the height of the flaw from the back surface of the specimen is detected, even the SPOD method, which is proposed by the inventors and disclosed in Non-Patent Document 3, cannot detect a signal due to attenuation because a beam path of a diffracted wave, which propagates above the flaw after it is reflected on the back surface of the specimen, is increased in length although the SPOD method makes use of the downward component of the diffracted wave from which a strongest energy can be obtained, wherein the above flaw includes a surface crack of a thick specimen such as the weld of a thick pipe and a corroded portion near a surface layer. The component, which propagates just downward, of the diffracted wave which expands in an arc-shape (spherical shape) is most strong. However, in the thick specimen, when an edge of a flaw is excessively away from the back surface of the specimen, for example, when the heights of a flaw located in the vicinity of the surface layer, an opening flaw of the front surface, and an opening flaw of the back surface are excessively high and away from the back surface, the diffracted wave reflected on the back surface of the specimen cannot return to a probe on a reception side, and thus an echo reflected from the bottom surface may not be observed. Accordingly, the SPOD method, which determines a flaw height from the difference between the arrival time of a component, which directly propagates above a flaw, of a diffracted wave generated in an edge of the flaw, and the arrival time of a component which propagates above the flaw after it is reflected once on back surface, may not determine the surface depth of a surface crack and the like. This is also the same in the diffracted wave generated in the interface between a corroded portion and a normal portion, and the diffracted wave, which propagates in the corroded portion and is reflected on a bottom surface, cannot be detected because it is greatly attenuated. That is, it cannot be observed on an oscilloscope.

Accordingly, an object of the present invention is to provide an ultrasonic flaw detection method and an ultrasonic flaw detection apparatus which can detect simply and accurately the position, the depth, and the height of an edge of a flaw, which includes a surface crack, a corroded portion near the surface layer of a thick specimen and a minute flaw.

Means for Solving the Problems

To achieve the object, as a result of various researches, the inventors have found that, in the components of a diffracted wave which is generated by the existence of a flaw, a component which returns to a source of incidence is weak, a component, which propagates to just below the flaw, that is, propagates to a back surface, i.e., bottom surface, side opposite to a front surface on which an ultrasonic wave is caused to be incident, is strongest, and a component which directly propagates above the flaw, i.e., on the front surface side of a specimen, is the second strongest. However, in a flaw in a front surface opening and a flaw located near the front surface of the specimen, a component, which directly propagates above the flaw is less attenuated because the propagation distance thereof is shorter than that of a component which propagates upward after it is reflected on the bottom surface once, with the result that the former component can be distinctly received as the strongest signal. Paying attention to the above fact, the inventors have determined the position, the flaw depth, or the flaw height of an edge of a flaw including a front surface crack, a corroded portion near the surface layer of a thick specimen, and a minute defect using a triangular method, i.e., Pythagorean theorem, from a beam path of an ultrasonic wave which directly propagates above the flaw as a diffracted wave after it reaches the flaw and the distance between the position of incidence and the position of detection of the ultrasonic wave on the front surface of a specimen or the difference between the propagation time to a normal probe for reception of a surface wave which reflects the above relation and the propagation time to the normal probe of the component of the diffracted wave which directly propagates above the flaw.

That is, an ultrasonic flaw detection method according to claim 1 causes an ultrasonic wave to be incident on a specimen by an angle probe from an oblique direction, detects a diffracted wave generated at an edge of a flaw in the specimen by a normal probe above the flaw, and determines the position of the edge of the flaw from the front surface of the specimen using a triangular method from a beam path of a component, which directly propagates above the flaw, of the diffracted wave, the beam path passing through the flaw between an angle probe for transmission and a normal probe for reception and the interval of the position of incidence and the position of detection of the ultrasonic wave, or from the difference between the propagation time of a surface wave, to which the above relations reflect, to the normal probe for reception and the propagation time of the diffracted wave, which directly propagates above the flaw, to the normal probe for reception. Since the relation between the beam path and the propagation time is shown by beam path=propagation time×speed of incident ultrasonic wave, when the propagation time can be detected in a material in which an ultrasonic wave is considered to have substantially a predetermined speed, the beam path can be determined by an arithmetic operation.

Further, since the ultrasonic flaw detection method of the present invention determines the position of an edge of a flaw making use of a component of the diffracted wave propagating toward a flaw detection surface, the method is suitable for determining the depth of a flaw from the front surface of a specimen or the height of the flaw from the back surface of the specimen in the situation in which it is difficult to detect a component of the diffracted wave which propagates to the position of an edge of a flaw, which includes a front surface crack, a corroded portion near the surface layer of a thick specimen, and a minute defect as well as propagates below the flaw (the surface on the opposite side of the surface on which an ultrasonic wave is incident) and propagates upward after it is reflected on a bottom surface once. When a flaw is a minute flaw, a beam path or the difference between propagation times is determined by causing an ultrasonic wave having a large amplitude to be incident as the ultrasonic wave and detecting the harmonic wave component of a diffracted wave which directly propagates upward from the minute flaw. Further, when a bottom surface on which a diffracted wave is reflected is away from an end of a flaw as a flaw near the surface layer of a specimen and a flaw in a front surface opening as a weld of a thick pipe and when the height of a flaw in a back surface opening is excessively high, the flaw height from a back surface can be determined from the difference between the thickness of the specimen measured by the ultrasonic flaw detection method and the thickness thereof measured by other method.

Further, the interval between the position of incidence and the position of detection of the ultrasonic wave may be detected from, for example, the propagation time of the surface wave, the interval between the angle probe for transmission and the normal probe for reception may be measured, or the position of incidence and the position of incidence of the ultrasonic wave on the front surface side of the specimen may be held to a predetermined interval.

Further, a piezoelectric vibrator and a magnetostrictive oscillator are ordinarily used as the ultrasonic wave generation source acting as the angle probe, the ultrasonic wave may be excited by a laser depending on a case. According to a laser ultrasonic wave method, since the ultrasonic wave is excited in a non-contact manner, it is preferable for measurement in a high temperature environment and measurement of a specimen having a complex shape and the like and further preferable when the height of a flaw is estimated from the relation of the propagation times of a surface wave and a diffracted wave that propagates above a flaw because the received signal of a strong surface wave exists as compared with an ultrasonic flaw detection method using a piezoelectric element. Here, when the laser is used as the angle probe, an interferometer is preferably used as the normal probe for reception. Further, in the laser ultrasonic wave method, it is preferable that the laser be composed of a plurality of lasers and a time lag be applied to the lasers by a delay generator to shift the intervals of radiation of the lasers so that generated ultrasonic waves reach an arbitrary one point at the same time to thereby control a propagation direction.

Further, the ultrasonic flaw detection apparatus according to the present invention includes an angle probe for transmission for causing an ultrasonic beam to be incident on a flaw in a specimen from an oblique direction, a normal probe for reception for receiving a diffracted wave propagating above the flaw, and an arithmetic operation unit for calculating the position of an edge of the flaw from the front surface of the specimen using a triangular method from the interval between a beam path of a component, which directly propagates above the flaw, of the diffracted wave which is received by the normal probe for reception and generated at the edge of the flaw, the beam path passing through the flaw between the angle probe for transmission and the normal probe for reception and the incident position and the detection position of the ultrasonic wave or from the difference between the propagation time of the surface wave to the normal probe for reception and the propagation time of the component of the diffracted wave directly propagating above the flaw to the normal probe for reception.

EFFECT OF THE INVENTION

According to the ultrasonic flaw detection method and apparatus of the present invention, since a component of the diffracted wave whose intensity follows that of a component of the diffracted wave propagating toward just below a flaw and which has a shortest beam path is directly received without passing through a wedge, the component of the diffracted wave is unlikely to be affected by attenuation and can be received as a stronger signal. Therefore, even an unskilled inspector can accurately measure a flaw without dispersion of measured results.

Further, according to the ultrasonic flaw detection method and apparatus of the present invention, even when a damage and the like exist in the vicinity of a surface layer of a specimen, the position from the front surface of the specimen to an edge of a flaw can be determined. Accordingly, the presence or absence of a flaw in the vicinity of the surface layer or the position of the flaw from the front surface or the back surface of the specimen, specifically, the depth of a surface flaw, the depth of a corroded flaw from the front surface, or the presence or absence of a closed flaw in the vicinity of the surface layer and the position thereof can be determined, and further the height of a back surface opening, and the like can be also determined from the known thickness of the specimen determined by another measurement method.

Moreover, according to the ultrasonic flaw detection method and apparatus of the present invention, the position of an edge of a flaw can be simply calculated. That is, it is possible to estimate the depth of a flaw on the front surface of a specimen without being affected by a material and the change in shape of a measurement surface.

According to the ultrasonic flaw detection method and apparatus of the present invention, since it is possible to detect a flaw in a specimen such as a blowhole in welding, the performance of a product can be evaluated by previously measuring these initial defects.

According to the ultrasonic flaw detection method of the present invention disclosed in claim 4, since the component of the diffracted wave which has a shortest distance, whose intensity follows that of the component of a diffracted wave directly propagating to the normal probe, and which directly propagates just below a flaw, is used, even a weak reflection source such as the interface between a healthy portion and a corroded portion in a specimen can receive the diffracted wave in the level and the intensity which can be detected. Accordingly, the position of the interface between the corroded portion and the healthy portion can be determined also using other measurement method and a visual judgment, and further the depth of a corroded portion from the front surface of the specimen or the height of the corroded portion from the back surface thereof can be determined.

Further, according to the ultrasonic flaw detection method of the present invention disclosed in claim 5, since the component of the diffracted wave which propagates upward in the shortest beam path is directly received without passing through a wedge, a harmonic wave component having a higher frequency can be received because it is unlikely to be affected by attenuation. That is, since the frequency of an ultrasonic wave for detection can be more increased than a conventional one, it has a high resolution for detection and a more minute flaw can be detected.

EXPLANATION OF REFERENCE NUMERALS

1 Ultrasonic flaw detection apparatus
2 Laser
3 Delay generator
6 Specimen
7 Interferometer
8 Detection laser
12 Personal computer
13 Front surface of specimen
14 Back surface of specimen
15 Surface wave
16 Ultrasonic wave incident on specimen
17 Diffracted wave
18 Diffracted wave propagating upward
21 Angle probe for transmission
22 Normal probe for reception
25 Corroded portion
26 Healthy portion
27 Interface between corroded portion and healthy portion

BEST MODE FOR CARRYING OUT THE INVENTION

An arrangement of the present invention will be explained below in detail based on an embodiment shown in the drawings.

An ultrasonic flaw detection method of the present invention causes an ultrasonic wave to be incident on a specimen by an angle probe from an oblique direction, detects a diffracted wave generated at an edge of a flaw in the specimen by a normal probe above the flaw, and determines the position of the edge of the flaw from the front surface of the specimen by a triangular method from a beam path of a component of the diffracted wave which directly propagates upward and passes through the flaw between the angle probe for transmission and the normal probe for reception and the interval between the incident position and the detection position of the ultrasonic wave or from the difference between the propagation time of a surface wave, to which the above relations reflect, to the normal probe for reception and the propagation time of the component of the diffracted wave, which directly propagates above the flaw, to the normal probe for reception.

The relation shown in Expression 2 is established between the beam path and propagation time.

$$\text{Beam path} = \text{propagation time} \times \text{speed of incident ultrasonic wave} \quad (2)$$

Figure 1:
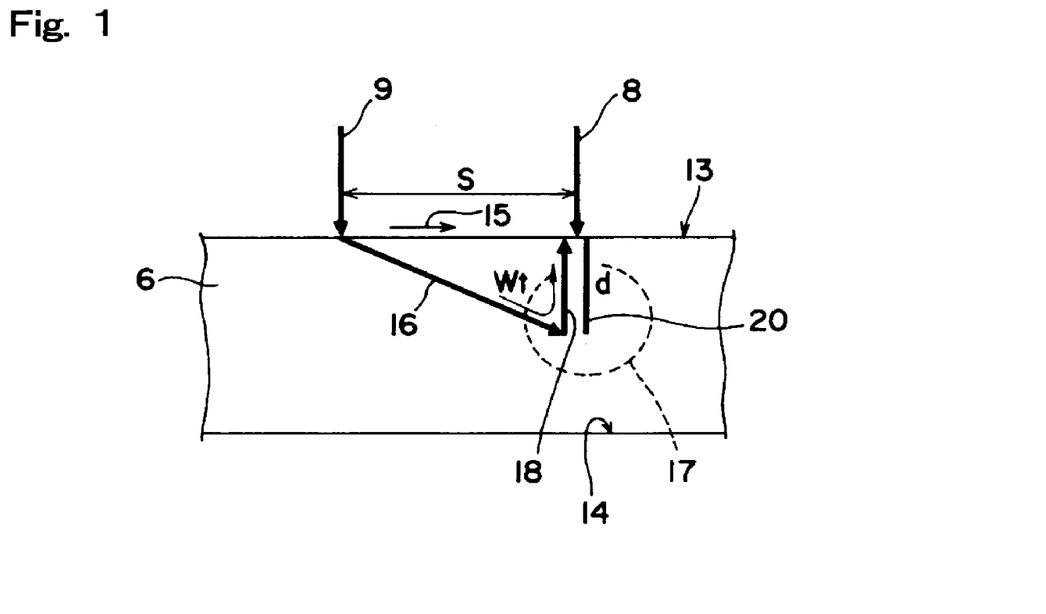
FIG. 1 is an explanatory view of flaw detection and a flaw depth estimation method according to an ultrasonic flaw detection method of the present invention.

Thus, when the propagation time can be detected in a material in which an ultrasonic wave is considered to have substantially a predetermined speed, the beam path Wt can be determined by an arithmetic operation. Further, as shown in FIG. 1, a component 18, which directly propagates just above a diffracted wave 17 generated at the edge of a flaw 20 and a surface wave 15 which propagates on the front surface 13 of a specimen 6 from the point of incidence of an ultrasonic wave toward the normal probe for reception (detecting position) has a relation of a rectangular triangle with respect to a beam 16 which reaches the flaw 20 from the point of incidence. From what has been described above, it is possible to determine the distance from the edge of the flaw to the front surface or the back surface of the specimen, that is, the depth or the height of the flaw, which includes a surface crack, a corroded portion near the surface layer of a thick specimen, and a minute damage, using the triangular method from the difference between the propagation time of the surface wave 15 propagating along the front surface 13 of the specimen and the propagation time of the ultrasonic wave 16 which propagates in the specimen 6 and generate the diffracted wave 17 in the flaw 20 or from the beam paths of the respective waves. Since the propagation distance of the component, which directly propagates just above the flaw of the diffracted wave, is shorter by the depth up to the flaw, it is less diffused and attenuated, thereby the diffracted wave can be accurately detected.

Here, it is preferable to use a longitudinal wave as a reception wave. This is because the longitudinal wave is unlikely to be affected by a metal structure due to its long wavelength in addition to the fact that it reaches a probe sooner than a shear wave. However, the wave used for detection is not limited to the longitudinal wave, and the shear wave may be used. The normal probe for reception can also receive the shear wave in addition to the longitudinal wave. It has been confirmed in an experiment that both the waves have a pinpoint accuracy and an excellent robust property. Accordingly, since the shear wave may be stronger depending on a detecting position, a flaw can be distinctly detected using any one or both of the longitudinal wave and the shear wave from which a better result of detection can be obtained.

Although a piezoelectric vibrator and a magnetostrictive oscillator are ordinarily used as the angle probe for transmission in the ultrasonic flaw detection method and apparatus, a laser may be also used depending on a situation. When an ultrasonic wave is excited using the laser, since the ultrasonic wave is excited in a non-contact manner, the laser is preferably used for measurement in a high temperature environment, measurement of a specimen having a complex shape, and the like. Further, the inventors have found that when an ultrasonic wave excited by laser is used, a received signal having a strong surface wave exists as compared with a case that the ultrasonic wave is caused to be incident using the piezoelectric element. As a result, since there exists the received signal having the strong surface wave as compared with an ultrasonic flaw detection method using the piezoelectric element, this is preferable for the case for determining the depth of a flaw from the front surface of a specimen or the height of the flaw from the back surface of the specimen using the triangular method, the flaw including a surface crack of a thick specimen, a corroded portion near the surface layer of the thick specimen, and a minute flaw. It is needless to say that an ordinary angle probe for transmission and an ordinary normal probe for reception using the piezoelectric vibrator, the magnetostrictive oscillator, and the like can detect a flaw without a problem. That is, any of the laser ultrasonic wave method and the ultrasonic flaw detection method using the piezoelectric element can detect a flaw depth accurately.

When the laser is used as the angle probe for transmission, it is effective and preferable to use an interferometer as the normal probe for reception for detecting the diffracted wave and to detect a flaw in a non-contact manner using the interferometer. When the ultrasonic vibration propagating in the specimen reaches the front surface thereof, the point of arrival vibrates in a minute displacement of nm or less. Thus, when a laser beam is radiated to the position at which the ultrasonic wave is desired to be detected, a minute light frequency transition, i.e., Doppler shift, is generated in the reflected light thereof. When the frequency and the phase of the laser beam are sufficiently stable, the minute light frequency transition can be measured using an interference effect. Note that when the laser is used as the angle probe, the interferometer is ordinarily used as the normal probe for reception. However, when a flaw can be detected in a contact state, the piezoelectric element and the magnetostrictive oscillator may be used as the normal probe for reception.

Figure 4:
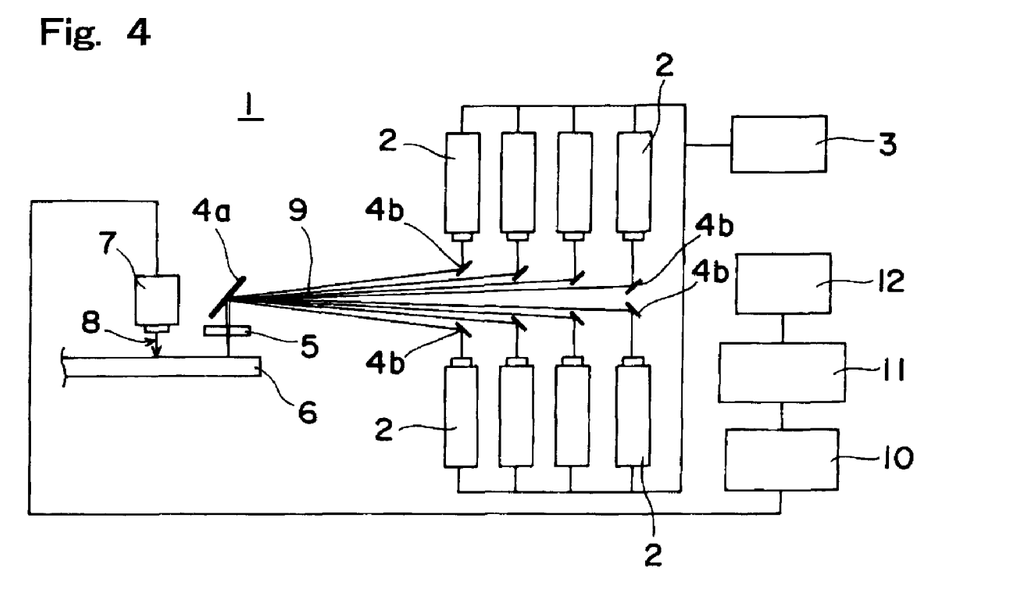
FIG. 4 is an explanatory view showing an example of an ultrasonic flaw detection apparatus for exciting an ultrasonic wave by a laser.

Further, when the ultrasonic wave is excited by radiating a laser to the specimen, it is preferable to control a propagating direction using a plurality of lasers 2 and applying a time lag so that the longitudinal wave or the shear wave of all of the ultrasonic waves, which are generated by shifting the timings at which the respective lasers 2 are radiated through a delay generator 3, reaches an arbitrary one point at the same time as shown in FIG. 4. In this case, the ultrasonic waves sequentially excited by the respective laser beams 9 that are radiated to the specimen 6 are synthesized, thereby an ultrasonic wave having a large amplitude can be formed. With this operation, a flaw can be accurately detected with a good sensitivity. Further, the propagating direction of the excited wave can be controlled by transmitting the laser beams 9 for excitation from the respective lasers 2 at a different timing and generating an ultrasonic wave. For example, when the time lag is set to a small value, the angle of incidence of the synthesized wave can be reduced, and when the time lag is set to a large value, the angle of incidence of the synthesized wave can be increased. Thus, the angle of incidence of the beams can be controlled by controlling the time lag. Further, an ultrasonic wave having a narrow band, in which energy is concentrated to the vicinity of a fundamental frequency, can be generated by controlling the order of arrival of the waves excited by the plurality of lasers 2 and integrating the waves.

A YAG laser having a Q switch, a $CO_2$ laser, an excimer laser, and the like can be used as the lasers 2 on the transmission side in the embodiment. Then, laser pulses are created with a time lag by setting the time lag of the Q switches of the respective lasers 2 on the transmission side by the delay generator 3 with respect to the trigger signal of a laser 8 for detection. Further, although it is preferable to use, for example, a mixed two-light-wave interferometer as an interferometer 7, it is not limited thereto, and other known or new interferometer such as a Fabry-Perot interferometer (CFPI) may be used. Further, a personal computer 12, which collects data and acts as a controller, is connected to the interferometer 7 through an oscilloscope 11 and a band pass filter 10. The signal detected by the interferometer 7 is recorded by the oscilloscope 11 through the band pass filter 10 and further inputted into the computer 12. The computer 12 includes a central processing unit (not shown), a program for prescribing an operation procedure of the central processing unit, a memory for storing the data etc. processed by the central processing unit, memory means for storing inputted data, display means, input means such as a keyboard and a mouse, and constructs a function corresponding to a flaw detector together with the oscilloscope 11 the band pass filter 10. Note that reference numerals 4a, 4b in the drawing denote mirrors, and a reference numeral 5 denotes a condenser lens. The band pass filter 10 is, for example, a low band pass filter and used to remove noise and the like.

According to the ultrasonic flaw detection apparatus arranged as described above, the process for applying the time lag so that the ultrasonic waves reach the arbitrary one point at the same time can be simply executed by, for example, monitoring the oscilloscope 11. Specifically, first, a waveform excited by one arbitrarily selected laser 2 is detected and recorded on a screen of the oscilloscope 11. Next, the remaining lasers 2 are sequentially excited one by one and the time lag is set to the lasers 2 while observing resulting waveforms on the oscilloscope 11 so that the resulting waveforms agree with the peak of waveforms recorded before them. It is needless to say that the time lag may be previously determined by a calculation using the triangular method. Further, the time lag of the laser may be previously determined to each of the thickness of the specimen 6, a material, an interval between the positions of radiation.

Figure 5:
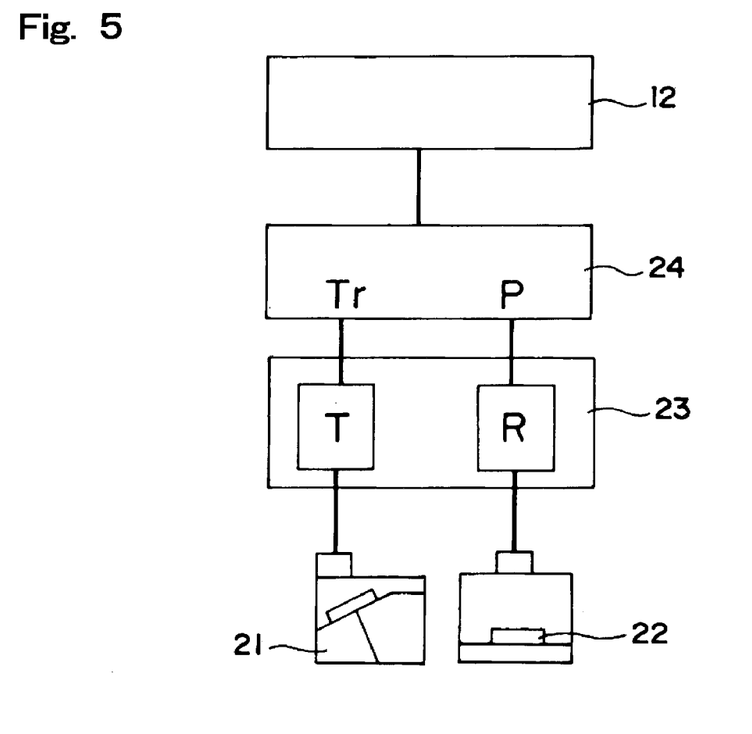
FIG. 5 is an explanatory view showing an example of an ultrasonic flaw detection apparatus using a piezoelectric vibrator.

Further, when the probe employing the piezoelectric element is used, the ultrasonic flaw detection method of the present invention can be executed by an apparatus having an arrangement exemplified in, for example, FIG. 5. The ultrasonic flaw detection apparatus has an angle probe 21 for transmission for causing an ultrasonic beam to be incident on the specimen 6, a normal probe 22 for reception for receiving a diffracted wave propagating above a flaw in the specimen 6, and a personal computer 12 which collects data and acts as a controller, and controls the transmitting operation and the receiving operation of the probe 21 for transmission and the probe 22 for reception through a pulse receiver 23 connected thereto through an A/D conversion board 24.

The computer 12, which performs the control operation and obtains the data, constitutes a function corresponding to the flaw detector by the A/D conversion board 24 and the pulse receiver 23. It is needless to say that a flaw detector may be separately used and the computer 12 only collects the data. Further, the computer 12 solely sets a scanning condition and controls a scan when a flaw is detected.

Note that, in any of the methods, the computer 12 calculates the position of an edge of the flaw 20 from the front surface 13 of the specimen 6 by the central processing unit using a triangular method from the entire beam path Wt of the incident ultrasonic wave 16 passing through the flaw 20 between the angle probe 21 for transmission and the normal probe 22 for reception of the component, which directly propagates above the flaw, of the diffracted wave 17 and the interval S between the position of incidence and the position of detection of the ultrasonic wave or from the difference $(t_t-t_s)$ between the propagation time of the incident ultrasonic wave 16, which is caused to be incident on the flaw 20, reaches the flaw 20, and directly propagates above the flaw 20 as a diffracted wave and the propagation time of the surface wave 15 in the specimen. At the same time, the difference between the arrival times to a flaw detection surface is shown by simultaneously displaying the surface wave 15 of the ultrasonic beam and the signal of the component 18 which directly propagates above the flaw of the diffracted wave 17 which is generated when the component 18 reaches the edge of the flaw 20 on the oscilloscope 11 as the display means.

FIG. 1 shows an explanatory view of an embodiment in which the ultrasonic flaw detection method is applied to measurement of the flaw depth of a surface crack. Note that the embodiment will be explained as to the case in which a laser is used as the probe on the transmission side and an interferometer and a laser for detection are used as the normal probe for reception.

In the embodiment, it is assumed that the position of radiation of the laser light 9 for excitation and the position of radiation of the laser light 8 for detection are moved in the same direction by the same amount while keeping a predetermined interval therebetween. In this case, a signal can be obtained only by integrally moving the position of radiation of the laser light 9 for excitation and the position of radiation of the laser light 8 for detection, a time is not taken to select the fixing position of one of the probes. Accordingly, when the position of radiation of the laser light 8 for detection reaches above the surface crack 20, the diffracted wave from the lower edge of the flaw 20 is detected. With this operation, it is possible to discover even a surface crack which cannot be visually discriminated. Note that it is needless to say that when the position of the surface crack 20 is previously known, the position of radiation of the laser 8 for detection may be determined as the position of the surface crack. When the interval S between the incident position and the detection position of the ultrasonic wave and the angle of incidence θ of the ultrasonic wave are set to predetermined values, the center of the ultrasonic beam, which expands in an arc-shape, does not always impinge on an extreme end of the flaw 20. However, even if a portion of the beam away from the center thereof impinges on the extreme end of the flaw 20, the diffracted wave is generated, and thus the extreme end of the flaw 20 can be detected. Further, the position of radiation of the laser light 9 for excitation may be scanned.

Figure 2:
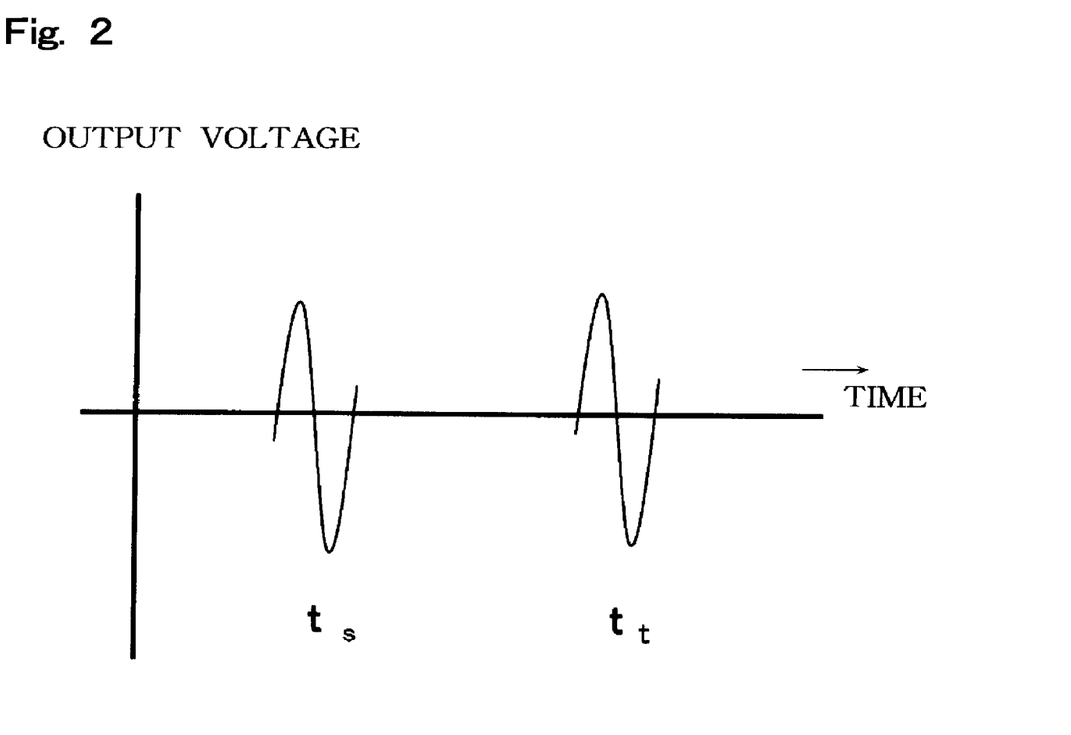
FIG. 2 is a view showing an example of the received waveforms of a surface wave and a diffracted wave when a flaw depth is estimated.

When the ultrasonic wave is caused to be incident, the normal probe 22 for reception first detects the surface wave 15 having a short beam path after a time $t_s$ passes and then detects the incident ultrasonic wave, which directly propagates above the flaw as a diffracted wave through the flaw 20 and has a beam path Wt after a time $t_t$ passes as shown in FIG. 2. When a sound speed is shown by C, the beam path Ws of the surface wave 15 and the entire beam path Wt of the ultrasonic wave in the specimen 6 are shown by $Ws=Ct_s$, $Wt=Ct_t$ by the relation of Expression 2 described above. From what has been described above, the flaw depth d of the surface crack 20 can be obtained from Expression 3 developed from Pythagorean theorem. Note that the interval S between the position of radiation of the laser light 9 for excitation and the position of radiation of the laser light 8 for detection, that is, the beam path Ws of the surface wave may be calculated from the propagation time of the surface wave 15, or the interval may be previously set to a predetermined value or may be actually measured each time a flaw is detected. Further, the sound speed C depends on the material of a specimen and can be previously determined.

$$d=(Wt^2-Ws^2)/2Wt \quad (3)$$

Figure 3:
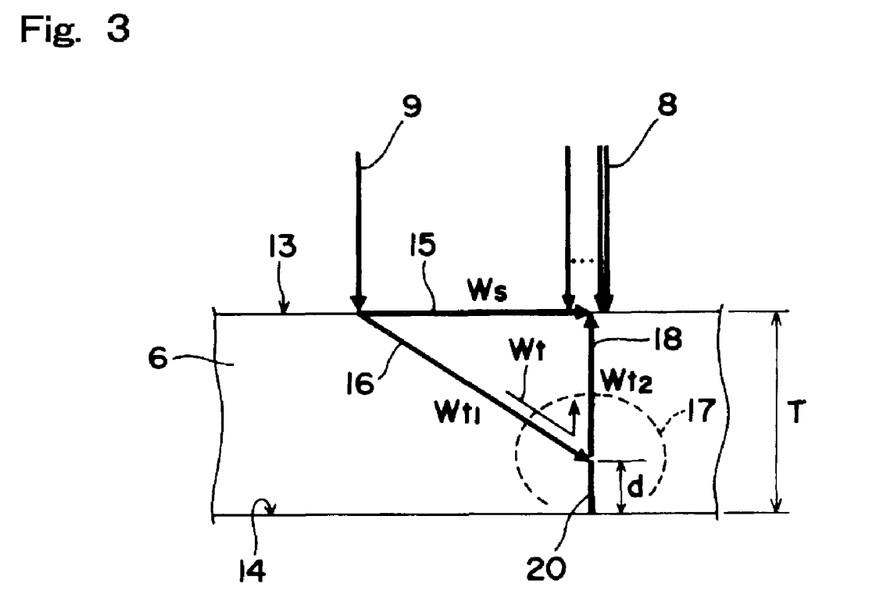
FIG. 3 is a view for explaining the flaw detection and the flaw depth estimation method according to the ultrasonic flaw detection method of the present invention.

Next, FIG. 3 shows a principle when the height d of a back surface flaw of a thick specimen is determined. The ultrasonic wave 16 whose propagation direction in the specimen 6 is controlled by the time lags set to the plurality of lasers 2 of the ultrasonic flaw detection apparatus 1 shown in FIG. 4 propagates up to the flaw 20 through a beam path $W_{t1}$ and further diffracted at an edge of the flaw 20 and generates the diffracted wave 17. The component 18 of the diffracted wave 17, which directly propagates just above the flaw 20, directly propagates up to the front surface 13 of the specimen 6 through a beam path $W_{t2}$. At the same time, the longitudinal surface wave 15 propagates to the vicinity of the front surface of the specimen 6 in the beam path Ws.

Expressions 4, 5 shown below are given from the arrival times $t_s$, $t_t$ of the surface wave 15 and the diffracted wave 18 which propagates above the incident ultrasonic wave 16.

$$Ws=C \cdot t_s \quad (4)$$

$$W_{t1}+W_{t2}=C \cdot t_t \quad (5)$$

Further, $W_{t2}$ can be determined from Expression 6, and the flaw height d can be determined by subtracting $W_{t2}$ from the thickness T of the specimen 6. Note that the thickness T of the specimen 16 can be simply measured by a thickness gauge and the like. Thus, even if the reflection of the diffracted wave 17 from the back surface 14 cannot be detected, when the distance $W_{t2}$ from the edge of a flaw in a back surface opening to the front surface 13 of the specimen can be determined, the height d of the flaw 20 from the back surface of the specimen can be determined.

$$W_{t2}=C(t_t-t_s^2)/2t_t \quad (6)$$

Figure 6:
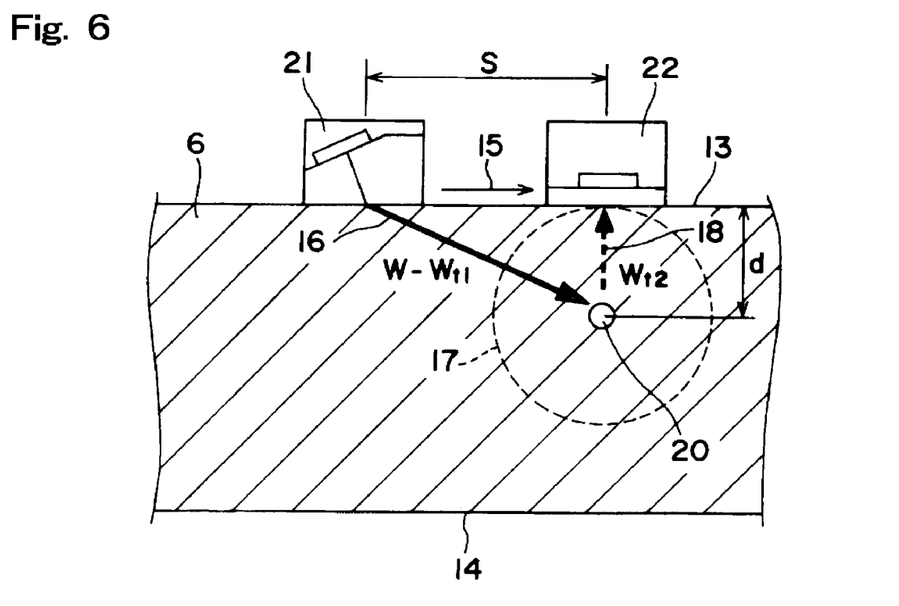
FIG. 6 is an explanatory view of an example of an embodiment in which a flaw in a specimen is detected.

Further, in the ultrasonic flaw detection method of the present invention, the existence of an edge of a flaw closed in the specimen, for example, a closed spherical defect such as a blowhole generated in welding the detection of which was conventionally difficult can be also detected likewise, and the depth position of the damage from the front surface of the specimen of the flaw can be estimated. In particular, as shown in FIG. 6, the ultrasonic flaw detection method of the present invention is useful when the flaw 20 exists in the vicinity of the surface layer of the specimen 6 or when the diffracted wave (not shown), which propagates to the front surface side of the specimen 6, that is, propagates upward after it is reflected once on the back surface 20 of the thick specimen 6 cannot be received because the flaw of the back surface opening has a long height.

That is, the position from the front surface 13 of the specimen to the edge of the flaw 20 can be determined by the method described above. In contrast, whether the flaw 20 is an open flaw or a closed defect can be simply discriminated by using the ultrasonic flaw detection method of the present invention together with other ultrasonic flaw detection method. When, for example, an angle flaw detection method is used, since a strong reflected wave from an opening is received as an opening echo, whether or not the flaw 20 is a closed defect can be determined by the presence or absence of the opening echo. Accordingly, it is possible to estimate the height position d of the defect 12 having an internal spherical portion such as a blowhole from the bottom surface the detection of which was difficult in a conventional ultrasonic flaw detection method, by combining the ultrasonic measurement method of the present invention and the angle flaw detection method.

Further, when an ultrasonic wave, which has a large amplitude that is at least five to ten times that of an ultrasonic wave (about 1 nm) used in an ordinary flaw detection test, is used in place of the above ultrasonic wave, a minute defect which exists in the specimen can be closed, and as a wave partially passes through a tensile phase of the ultrasonic wave, a harmonic wave component is generated to the diffracted wave 17 (nonlinear property of the diffracted wave). Accordingly, the normal probe 2 for reception receives the diffracted wave including the harmonic wave component. For example, when the ultrasonic wave having a frequency of 5 MHz is caused to be incident, the normal probe 22 for reception receives a second-order harmonic wave of 10 MHz. Thus, whether or not a minute flaw exists in the specimen can de determined, that is, the minute defect can be detected depending on whether a harmonic wave component is included in the received diffracted wave 18. Further, the position of the minute flaw 20 from the front surface of the specimen can be estimated from the difference between the arrival time of the diffracted wave 18 which directly propagates upward from the minute flaw 20 and the arrival time of the surface wave 15. In this case, since the ultrasonic wave having the large amplitude can detect a more minute flaw as the ultrasonic wave has a higher frequency, it is preferable to use an ultrasonic wave having a higher frequency in the range in which the normal probe for reception can receive the ultrasonic wave.

Since the ultrasonic wave having the large amplitude has a larger attenuation than an ordinary ultrasonic wave. Thus, when the ultrasonic wave has a long propagation distance, since it is diffused and attenuated, a harmonic wave component having a signal level, which can be received by the normal probe for reception, cannot be detected. However, in the present invention, when the diffracted wave 18, which propagates directly upward from the extreme end of the flaw 20, that is, propagates to the normal probe 22 for reception, is directly received by the normal probe 22 for reception without using a wedge, the diffracted wave 18 can be received while keeping the strong signal thereof and minimizing the attenuation thereof. Accordingly, when a present ordinary wedge is used, the normal probe for reception can receive a second-order harmonic wave having 16 MHz at the maximum.

Note that when it is intended to detect only whether or not the minute flaw 14 exists, it is only necessary for the normal probe 22 for reception to receive at least the diffracted wave 18 and the harmonic wave component thereof.

Figure 7:
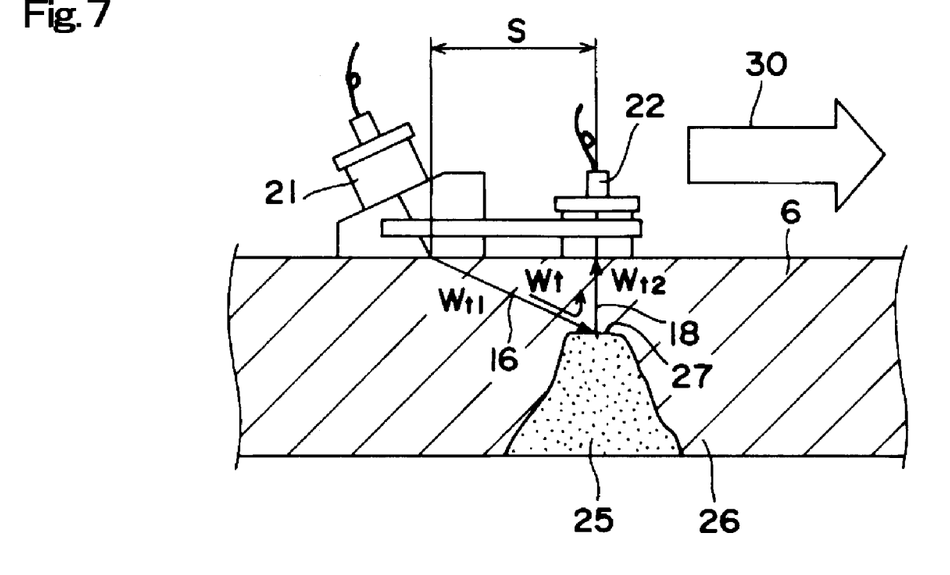
FIG. 7 is a view for explaining a principle of detection of the interface of a back surface corroded portion in the specimen.

Further, the ultrasonic flaw detection method of the present invention can be also applied when the interface 27 between a healthy portion 26 and a corroded portion 25 in the specimen 6 is detected. For example, as shown in FIG. 7, the interface 27 can be detected with a minimum attenuation by causing the ultrasonic wave 16 to be incident from the angle probe 21 for transmission and capturing the weak diffracted wave 18, which propagates upward from the interface 27, of the diffracted wave 17 generated on the interface 27, in a short beam path. Note that, in the ultrasonic flaw detection method, an ultrasonic wave having an ordinary amplitude may be used or an ultrasonic wave having a large amplitude may be used so as to use a nonlinear ultrasonic wave as the incident wave 16. Further, when minute defects are generated in the specimen as a group, the position of the group can be determined as a corroded and deteriorated portion (hereinafter, called a corroded portion).

Figure 8:
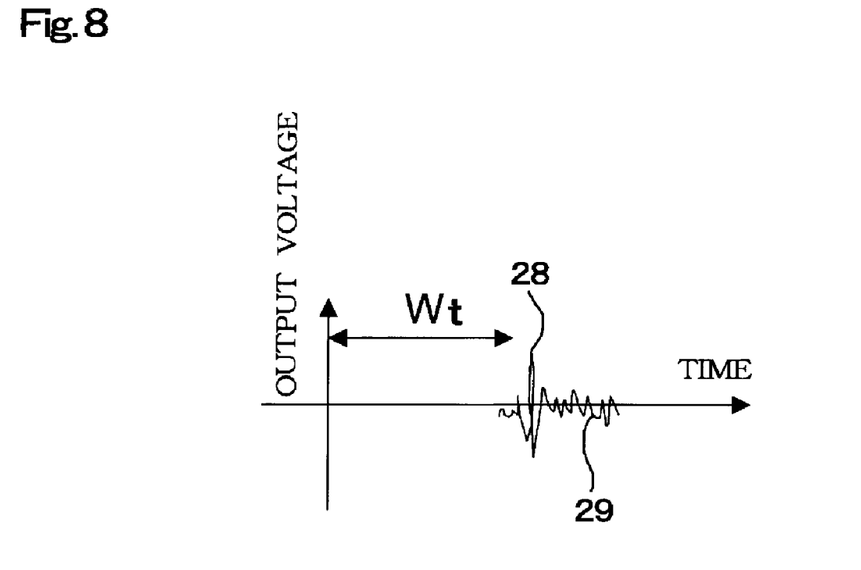
FIG. 8 is a graph showing an example of a received waveform in the detection method of FIG. 7, wherein a vertical axis shows displacement and a lateral axis shows a beam path.

When a waveform is observed while scanning the angle probe 21 for transmission in an arrow direction in the drawing with the normal probe 22 for reception fixed on the corroded portion 25, a received waveform as shown in FIG. 8 can be obtained if the interface 27 exists. The peak 28 of a displacement shows the diffracted wave 18 from the interface 27, and a continuous displacement after the peak 28 shows a dispersed wave 29 from the back surface 14. Note that, although it is assumed in the embodiment that the angle probe 21 for transmission and the normal probe 22 for reception are moved while keeping the predetermined interval therebetween, the interval between the two probes may be measured each time it is necessary. Note that, as shown in FIG. 8, when the dispersed wave 29 appears after the peak 28, it can be confirmed that the corroded portion exists on the back surface.

Figure 9:
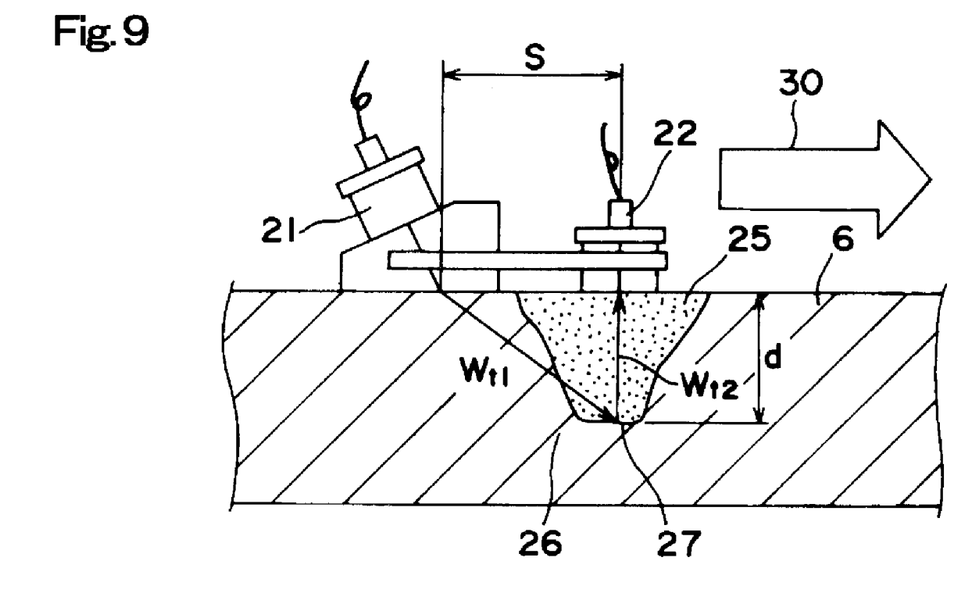
FIG. 9 is a view showing a principle of detection of the interface of a front surface corroded portion in the specimen.
Figure 10:
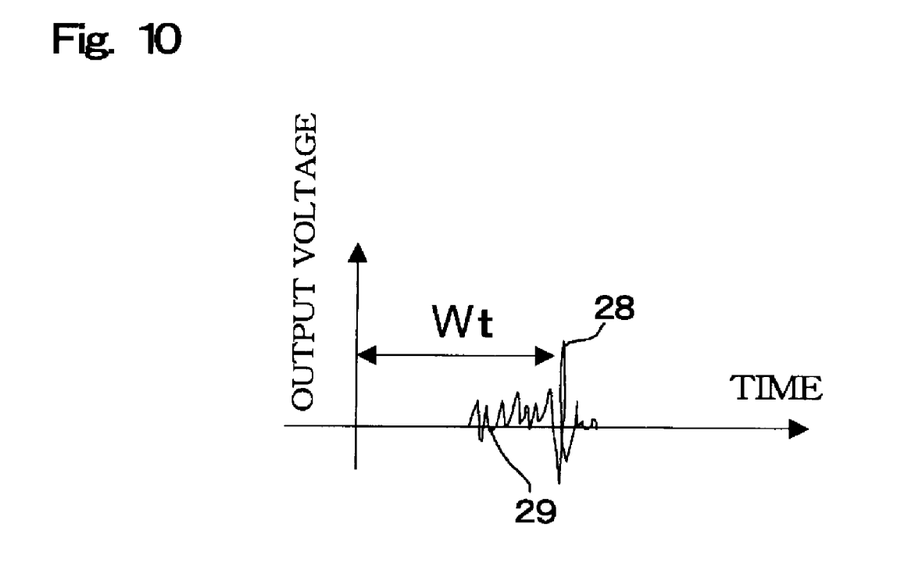
FIG. 10 is a graph showing an example of a received waveform in the detection method of FIG. 9, wherein a vertical axis shows displacement and a lateral axis shows a beam path.

On the contrary, when the corroded portion 25 exists on the surface layer of the specimen 6 as shown in FIG. 9, a received waveform as shown in FIG. 10 is exhibited, and the depth $T_1$ of the interface 27 thereof can be determined by the triangular method as described above. Here, when the surface corrosion exists, first, the dispersed wave 29 from the interface 27 is received, and thereafter the peak 28 of the diffracted wave 18 from the interface 27 is received. Accordingly, whether a corrosion is a front surface corrosion generated on the front surface or a back surface corrosion generated on the back surface can be determined depending on which of the dispersed wave 29 and the peak 28 appears first.

Note that the embodiment described above is a preferable embodiment of the present invention, the present invention is not limited thereto and can be variously modified and embodied within the scope which does not depart from the gist of the present invention. For example, an electromagnetic ultrasonic probe (EMAT) making use of a Lorenz force may be used as the probe. Further, when an ultrasonic wave is excited to the specimen by a laser, a flaw may be detected by installing the specimen 6 in water (water dipping method).

Further, although it is most preferable to dispose the normal probe 22 for reception just above the flaw 20, it is not strictly limited to the just above position, and it is possible to appropriately shift the position of the normal probe 22 within the range in which the diffracted wave 18 directly propagating above the flaw 20 can be received according to a situation.

Further, when a flaw detection surface on which the probes 21, 22 are placed has an irregular portion, for example, an weld reinforcement, a deformed surface, an unpolished portion, and the like, the probes, in particular, the normal probe 22 for reception that uses no wedge is not caused to come into intimate contact with the flaw detection surface. Therefore, it is preferable to use a probe which has flexibility to the flaw detection surface. As the flexible probe 7, a soft probe manufactured by Japan Probe and the like, for example, can be used.

Further, it is also possible to perform transmission and reception in the state that a water vessel is disposed around any one or both of the probes for transmission and reception and they are dipped in water. Note that a partial water dipping method can be also used by the probe on the transmission side by changing the angle thereof in water.

EXAMPLES

Example 1

An experiment was performed to confirm whether or not the ultrasonic flaw detection method of the present invention is useful. In this experiment, an aluminum specimen 6 having a polished front surface, a width of 40 mm, a length of 80 mm, and a thickness of 20 mm was used. Note that, in the experiment, slits 20 having a width of 0.5 mm and heights of 2 mm, 5 mm, and 8 mm were formed in the specimen 6 in place of flaws. In the experiment, an ultrasonic wave was excited using a single laser. Note that the angle of incidence of the longitudinal wave ultrasonic wave was controlled to 45°.

Since the specimen 6 was as thin as 20 mm, the slits could not be detected by a laser for detection. To cope with this problem, a normal probe 22 for reception composed of a piezoelectric element having a basic frequency of 5 MHz and a diameter of 8 mm was used.

Figure 11:
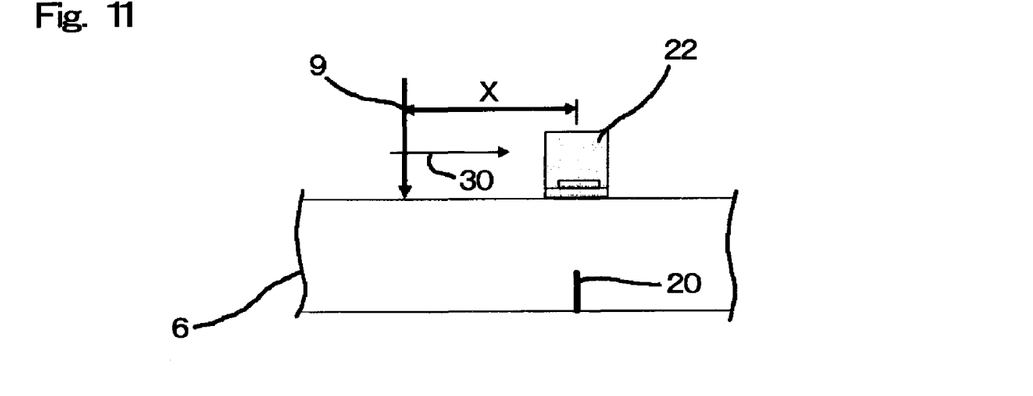
FIG. 11 is an explanatory view showing a method of detecting an edge of a flaw in the specimen while moving a position to which an excitation laser is radiated in the state that a probe on a reception side is fixed above a slit.
Figure 12:
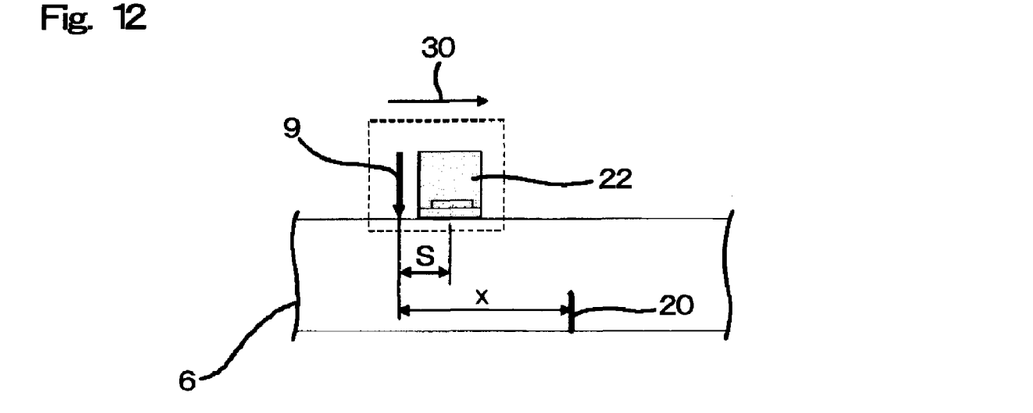
FIG. 12 is an explanatory view showing a method of detecting an edge of a flaw in the specimen being inspected while simultaneously moving a probe for reception and the position to which the excitation laser is radiated with the interval between the probe and the position kept constant.

Scan was performed by two scan methods as shown in FIGS. 11 and 12. As shown in FIG. 11, one of the methods was such that the normal probe 22 for reception was previously disposed fixedly above the slit 20, and the position of radiation of a laser light 9 for excitation on a transmission side was moved. As shown in FIG. 12, the other method was such that a predetermined interval S was set between the respective positions of radiation of the normal probe 22 for reception and the laser light 9 for excitation, and the laser light 9 for excitation and the normal probe 22 for reception were moved together at the same time in the same amount in the same direction. Note that x shows the distance between the position of radiation of the laser and the slit 20 when the scan started, and S shows the distance between the position of radiation of the laser and the position of the probe 22 for reception. Note that, the scan was performed at a pitch of 1 mm. Further, an arrow denoted by reference numeral 30 shows a scan direction.

Table 1 shows results of the flaw detection. In the flaw detection method using a surface wave and an upper diffracted wave, when the slit 20 is 2 mm or 5 mm high, no error is caused, and even if the slit 20 is 8 mm high, an error is only 0.4 mm (error of 5%), from which it can be confirmed that the height of a flaw can be measured with a high accuracy. As described above, according to the ultrasonic flaw detection method of the present invention, it can be confirmed that the measurement accuracy of the height of a flaw can be increased.

TABLE 1

| Slit length (mm) | Method of using surface wave and upper diffracted wave | |
| --- | --- | --- |
| | Result of measurement (mm) | Error (mm) |
| 2.0 | 2.0 | 0.0 |
| 5.0 | 5.0 | 0.0 |
| 8.0 | 8.4 | 0.4 |

The invention claimed is:

1. An ultrasonic flaw detection method comprising:
   causing an ultrasonic wave to be incident on a specimen by an angle probe from an oblique direction;
   detecting a diffracted wave generated at an edge of a flaw in the specimen by a normal probe above the flaw; and
   determining the position of the edge of the flaw from the front surface of the specimen using a triangular method from a beam path of a component of the diffracted wave which directly propagates upward and passes through the flaw between the angle probe for transmission and the normal probe for reception and an interval between the incident position and the detection position of the ultrasonic wave or from the difference between the propagation time of a surface wave to the normal probe for reception and the propagation time of the component of the diffracted wave, which directly propagates above the flaw, to the normal probe for reception.

2. The ultrasonic flaw detection method according to claim 1, wherein the flaw is a surface crack, and the depth of the flaw from the front surface of the specimen is determined.

3. The ultrasonic flaw detection method according to claim 1, wherein the flaw is a damage in the specimen, and the position of depth of the damage from the front surface of the specimen is determined.

4. The ultrasonic flaw detection method according to claim 1, wherein the flaw is a corroded portion, and the depth or height of an interface between a healthy portion and the corroded portion in the specimen from the front surface or the back surface of the specimen is determined.

5. The ultrasonic flaw detection method according to claim 1, wherein the flaw is a minute damage, an ultrasonic having a large amplitude is caused to be incident as the ultrasonic wave, and the beam path or the propagation time of the diffracted wave component is determined by detecting a harmonic wave component of the diffracted wave which directly propagates upward from the minute flaw.

6. The ultrasonic flaw detection method according to claim 1, further comprising:
   detecting a surface wave propagating on the front surface of the specimen and the diffracted wave component diffracting upward from the edge of the flaw;
   determining the position of the edge of the flaw from the front surface of the specimen from the difference between the propagation time of surface wave and the propagation time of the diffracted wave component using the triangular method; and
   determining the height of a flaw of a back surface opening or a flaw in the specimen from the back surface based on the difference from the thickness of the specimen.

7. The ultrasonic flaw detection method according to claim 1, wherein the interval between the incident position of the ultrasonic wave and the detection position of the ultrasonic wave is detected from the propagation time of the surface wave.

8. The ultrasonic flaw detection method according to claim 1, wherein the interval between the incident position of the ultrasonic wave and the detection position of the ultrasonic wave is previously determined and held to a predetermined interval.

9. The ultrasonic flaw detection method according to claim 1, wherein the angle probe is a laser.

10. The ultrasonic flaw detection method according to claim 9, wherein the laser is composed of a plurality of lasers, and a time lag is applied so that generated ultrasonic waves simultaneously reach an arbitrary one point by shifting the radiation intervals of the lasers through a delay generator, thereby controlling the propagation direction.

11. An ultrasonic flaw detection apparatus comprising:
    an angle probe for transmission for causing an ultrasonic beam to be incident on a flaw in a specimen from an oblique direction;
    a normal probe for reception for receiving a diffracted wave propagating above the flaw; and
    an arithmetic operation unit for calculating the position of an edge of the flaw from the front surface of the specimen using a triangular method from a beam path of a component, which directly propagates above the flaw, of the diffracted wave which is received by the normal probe for reception and generated at the edge of the flaw, the beam path passing through the flaw between the angle probe for transmission and the normal probe for reception, and an interval between the incident position and the detection position of the ultrasonic wave or from the difference between the propagation time of a surface wave to the normal probe for reception and the propagation time of the component of the diffracted wave directly propagating above the flaw to the normal probe for reception.

* * * * *